United States Patent
Suzuki et al.

(10) Patent No.: US 7,932,289 B2
(45) Date of Patent: *Apr. 26, 2011

(54) REMEDY FOR DIABETES

(75) Inventors: Nobuhiro Suzuki, Tsukuba (JP); Masami Suzuki, Osaka (JP); Tomoko Asakawa, Osaka (JP); Osamu Kataoka, Osaka (JP)

(73) Assignee: Takeda Pharmaceutical Company Limited, Osaka (JP)

( * ) Notice: Subject to any disclaimer, the term of this patent is extended or adjusted under 35 U.S.C. 154(b) by 747 days.

This patent is subject to a terminal disclaimer.

(21) Appl. No.: 11/658,450

(22) PCT Filed: Jul. 26, 2005

(86) PCT No.: PCT/JP2005/013995
§ 371 (c)(1),
(2), (4) Date: Feb. 23, 2007

(87) PCT Pub. No.: WO2006/011615
PCT Pub. Date: Feb. 2, 2006

(65) Prior Publication Data
US 2008/0319077 A1    Dec. 25, 2008

(30) Foreign Application Priority Data

Jul. 27, 2004 (JP) ................. 2004-218736

(51) Int. Cl.
*A61K 31/19* (2006.01)
(52) U.S. Cl. ....................... 514/568; 514/866
(58) Field of Classification Search ............. 514/183, 514/866, 568
See application file for complete search history.

(56) References Cited

U.S. PATENT DOCUMENTS

| | | | |
|---|---|---|---|
| 7,456,218 B2 * | 11/2008 | Yasuma et al. ........ | 514/568 |
| 2006/0100261 A1 | 5/2006 | Hamamura et al. | |
| 2006/0148858 A1 | 7/2006 | Maekawa et al. | |
| 2006/0258722 A1 | 11/2006 | Yasuma et al. | |

FOREIGN PATENT DOCUMENTS

| | | |
|---|---|---|
| EP | 1 559 422 A1 | 8/2005 |
| EP | 1 671 649 A1 | 6/2006 |
| EP | 1 698 624 A1 | 9/2006 |
| EP | 1 726 580 A1 | 11/2006 |
| EP | 1 731 505 A1 | 12/2006 |
| WO | WO 02/057783 A2 | 7/2002 |
| WO | WO 03/099793 A1 | 12/2003 |
| WO | WO 2004/022551 A1 | 3/2004 |
| WO | WO 2004/041266 A1 | 5/2004 |
| WO | WO 2004/106276 A1 | 12/2004 |
| WO | WO 2005/032590 A1 | 4/2005 |
| WO | WO 2005/063725 A1 | 7/2005 |
| WO | WO 2005/063729 A1 | 7/2005 |
| WO | WO 2005/087710 A1 | 9/2005 |
| WO | WO 2005/095338 A1 | 10/2005 |

OTHER PUBLICATIONS

Fanhanel et al., "Metformin's Effects on Glucose and Lipid Metabolism in Patients with Secondary Failure to Sulfonylureas," Diabetes Care, vol. 19, No. 11, Nov. 1996, pp. 1185-1189.

Kan et al., "The effect of ultra-rapid-acting insulin secretagogue, nateglinide (Na), in patients with type 2 diabetes that seems to be secondary ineffectiveness of SU drugs," The Journal of the Japan Diabetic Society, 2000, vol. 43 (Suppl. 1), p. S-120 (with English translation).

Kiyono et al., "Analysis of functional relation of pancreatic β-cell ATP-sensitive $K^+$ channels and sulfonylurea receptor, and development of oral antidiabetic drug based on new action mechanism," Research Papers of the Suzuken Memorial Foundation, 1999, Suzuken Memorial Foundation, 2001, pp. 147-149 (with English translation).

Mimura et al., "Experience of use of rapid-acting postprandial hypoglycemic drug (nateglinide) in type 2 diabetic patients who showed secondary effectiveness of sulfonylurea drugs," Nippon Taishaitsugaku Zasshi, 2001, vol. 63(1-2), p. 52 (with English translation).

Trischitta et al., "Comparison of Combined Therapies in Treatment of Secondary Failure to Glyburide," Diabetes Care, vol. 15, No. 4, Apr. 1992, pp. 539-542.

Uemura et al., "Usefulness of thiazolidine derivative in secondary failure to sulfonylurea drugs," Journal of Japan Diabetic Society, 2001, vol. 44, No. 3, p. 256, 2-S 2-4 (with English translation).

Yamada, Kentaro, "New Strategy of Oral Drug Therapy," Tonyobyogaku no Shinpo, 2002, vol. 36, pp. 292-296 (with English translation).

* cited by examiner

*Primary Examiner* — Kevin Weddington
(74) *Attorney, Agent, or Firm* — Foley & Lardner LLP

(57) ABSTRACT

The present invention relates to a therapeutic agent for diabetes with sulfonylurea secondary failure, which contains a GPR40 agonist. According to the present invention, a therapeutic agent for diabetes with sulfonylurea secondary failure that affords a superior insulin secretion effect and a superior hypoglycemic effect even in diabetic patients for whom a sulfonylurea compound or a fast-acting insulin secretagogue fails to provide an insulin secretion effect and therefore, fails to provide a sufficient hypoglycemic effect can be provided.

5 Claims, No Drawings

REMEDY FOR DIABETES

TECHNICAL FIELD

The present invention relates to a therapeutic agent for diabetes with sulfonylurea secondary failure, which contains a GPR40 agonist.

BACKGROUND ART

Sulfonylurea compounds (hereinafter sometimes to be abbreviated as SU agent) have been widely used as a first-line agent of an oral hypoglycemic agent. However, a condition where a sufficient hypoglycemic effect cannot be obtained when an SU agent is repeatedly administered to diabetic patients, namely, sulfonylurea secondary failure, occurs.

Since a treatment effect by the administration of an SU agent cannot be expected in diabetic patients with sulfonylurea secondary failure, they are treated with insulin preparations.

On the other hand, GPR40 agonists are known to be useful as a therapeutic agent for diabetes and the like (see, for example, the following patent documents 1-5).
patent document 1: WO03/099793
patent document 2: WO2004/022551
patent document 3: WO2004/041266
patent document 4: WO2004/106276
patent document 5: WO2005/051890

DISCLOSURE OF THE INVENTION

An object of the present invention is to provide a therapeutic agent for diabetes with sulfonylurea secondary failure, which affords a superior insulin secretion effect and a superior hypoglycemic effect, even in diabetic patients for whom a sulfonylurea compound or a fast-acting insulin secretagogue fails to provide an insulin secretion effect and therefore, fails to provide a sufficient hypoglycemic effect.

The present inventors have conducted intensive studies and first found that a GPR40 agonist is useful as a therapeutic agent for diabetes with sulfonylurea secondary failure, which resulted in the completion of the present invention.

That is, the present invention relates to
1) a therapeutic agent for diabetes with sulfonylurea secondary failure, which comprises a GPR40 agonist (hereinafter sometimes to be abbreviated as the agent of the present invention);
2) the agent of the aforementioned 1), wherein the sulfonylurea secondary failure is caused by a sulfonylurea compound;
3) the agent of the aforementioned 1), wherein the sulfonylurea secondary failure is caused by a fast-acting insulin secretagogue;
4) the agent of the aforementioned 1), wherein the GPR40 agonist is a compound comprising an aromatic ring and a group that releases a cation;
5) the agent of the aforementioned 1), wherein the GPR40 agonist is a compound represented by the formula:

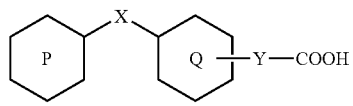

(I)

wherein ring P is an aromatic ring optionally having substituent(s), ring Q is an aromatic ring optionally further having substituent(s) besides —Y—COOH, and X and Y are each independently a spacer, or a salt thereof or a prodrug thereof;
6) use of a GPR40 agonist for the production of a therapeutic agent for diabetes with sulfonylurea secondary failure;
7) a method for treating diabetes with sulfonylurea secondary failure in a mammal, which comprises administering an effective amount of a GPR40 agonist to the mammal;
and the like.

The therapeutic agent for diabetes with sulfonylurea secondary failure of the present invention affords a superior insulin secretion effect and a superior hypoglycemic effect, even in diabetic patients for whom a sulfonylurea compound or a fast-acting insulin secretagogue fails to provide an insulin secretion effect and therefore, fails to provide a sufficient hypoglycemic effect.

When compared with the insulin preparations currently used as therapeutic agents for diabetes with sulfonylurea secondary failure, the agent of the present invention is a safe pharmaceutical agent free of side effects (e.g., vascular complication, hypoglycemia) induced by the administration (particularly long-term administration) of insulin preparations.

Moreover, by the administration of the agent of the present invention to diabetic patients with sulfonylurea secondary failure under treatment with an insulin preparation, the dose of the insulin preparation can be reduced.

BEST MODE FOR EMBODYING THE INVENTION

In the present specification, the GPR40 agonist may be any compound as long as it has an agonist activity (activating action) on a GPR40 receptor. While the compound may be peptidic or nonpeptidic, it is preferably nonpeptidic.

In addition, the GPR40 agonist may have different forms before and after administration to a living organism, as long as it maintains an agonist activity on a GPR40 receptor. That is, the GPR40 agonist may be an "active metabolite" having an agonist activity on a GPR40 receptor after conversion to a substance with a different structure after metabolism in vivo. Moreover, the GPR40 agonist may be a "prodrug" that is converted to an active form by a reaction with enzyme, gastric acid and the like under physiological conditions in the living body.

Specific examples of the GPR40 agonist include the following (1) to (7).
(1) A compound described in WO2004/041266, comprising an aromatic ring and a group that releases a cation, preferably a carboxylic acid comprising an aromatic ring or a derivative thereof, more preferably a compound represented by the formula:

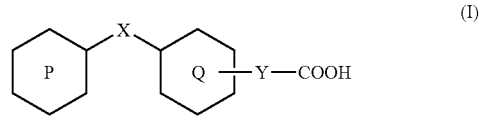

(I)

wherein ring P is an aromatic ring optionally having substituent(s), ring Q is an aromatic ring optionally further having substituent(s) besides —Y—COOH, and X and Y are each independently a spacer (hereinafter sometimes to be abbreviated as compound (I)) or a salt thereof or a prodrug thereof.

As an aromatic ring represented by ring P and ring Q, for example, an aromatic hydrocarbon ring and an aromatic heterocycle can be mentioned.

As the aromatic hydrocarbon ring, for example, an aromatic hydrocarbon ring having 6 to 14 carbon atoms such as a benzene ring, a naphthalene ring and the like can be used.

As the aromatic heterocycle, a 5- to 14-membered monocyclic, bicyclic or tricyclic aromatic heterocycle containing, besides a carbon atom, one or two kinds of 1 to 4 hetero atoms selected from a nitrogen atom, a sulfur atom and an oxygen atom, can be used. As the aromatic heterocycle, for example, aromatic heterocycles such as thiophene, furan, oxazole, benzo[b]thiophene, benzo[b]furan, benzimidazole, benzoxazole, benzothiazole, benzisothiazole, naphtho[2,3-b]thiophene, pyrrole, imidazole, pyrazole, pyridine, pyrazine, pyrimidine, pyridazine, indole, isoindole, 1H-indazole, purine, 4H-quinolizine, isoquinoline, quinoline, phthalazine, naphthyridine, quinoxaline, quinazoline, cinnoline, carbazole, β-carboline, phenanthridine, acridine, phenazine, thiazole, isothiazole, phenothiazine, isoxazole, furazan, phenoxazine and the like, a ring formed by condensation of these rings with 1 or 2 aromatic rings (e.g., benzene ring), and the like are used.

As the substituents that the aforementioned ring P and the aforementioned ring Q optionally have, for example, oxo group; halogen atom; $C_{1-3}$ alkylenedioxy group; nitro group; cyano group; optionally esterified carboxyl group; optionally substituted $C_{1-6}$ alkyl group; optionally substituted $C_{2-6}$ alkenyl group; optionally substituted $C_{2-6}$ alkynyl group; optionally substituted $C_{3-8}$ cycloalkyl group; optionally substituted $C_{1-6}$ alkoxy group; hydroxy group; mercapto group; optionally substituted $C_{1-6}$ alkylthio group; formyl group; optionally substituted $C_{1-6}$ alkyl-carbonyl group; optionally substituted $C_{3-8}$ cycloalkyl-carbonyl group; $C_{1-6}$ alkylsulfonyl group; $C_{1-6}$ alkylsulfinyl group; formylamino group; optionally substituted $C_{1-6}$ alkyl-carbonylamino group; optionally substituted $C_{3-8}$ cycloalkyl-carbonylamino group; optionally substituted $C_{1-6}$ alkoxy-carbonylamino group; optionally substituted $C_{1-6}$ alkylsulfonylamino group; optionally substituted $C_{1-6}$ alkyl-carbonyloxy group; optionally substituted $C_{1-6}$ alkoxy-carbonyloxy group; optionally substituted mono-$C_{1-6}$ alkyl-carbamoyloxy group; optionally substituted di-$C_{1-6}$ alkyl-carbamoyloxy group; sulfo group; sulfamoyl group; sulfinamoyl group; sulfenamoyl group; optionally substituted 5- to 7-membered heterocyclylcarbonyl group containing, besides a carbon atom, one or two kinds of 1 to 4 hetero atoms selected from a nitrogen atom, a sulfur atom and an oxygen atom; optionally substituted $C_{6-14}$ aryloxy group; optionally substituted $C_{7-16}$ aralkyloxy group; optionally substituted $C_{6-14}$ arylthio group; optionally substituted $C_{7-16}$ aralkylthio group; optionally substituted $C_{6-14}$ aryl-carbonyl group; optionally substituted $C_{7-16}$ aralkyl-carbonyl group; optionally substituted $C_{6-14}$ aryl-carbonylamino group; optionally substituted $C_{6-14}$ aryl-carbonyloxy group; optionally substituted mono- or di-$C_{6-14}$ aryl-carbamoyloxy group; optionally substituted $C_{6-14}$ arylsulfonyl group; optionally substituted $C_{6-14}$ arylsulfinyl group; optionally substituted $C_{6-14}$ arylsulfonylamino group; optionally substituted aromatic heterocyclyloxy group; optionally substituted $C_{6-14}$ aryl group; optionally substituted $C_{7-16}$ aralkyl group; optionally substituted $C_{6-14}$ aryl-$C_{2-6}$ alkenyl group; optionally substituted heterocyclic group; thiocarbamoyl group; optionally substituted carbamoyl group; optionally substituted amino group; and the like can be mentioned. The number of these substituents is preferably 1 to 3.

As the spacer represented by X or Y, for example, an alkylene group (preferably $C_{1-13}$ alkylene group) optionally having substituent(s) or an alkenylene group (preferably $C_{2-13}$ alkenylene group) optionally having substituent(s), wherein —C— of the alkylene group or alkenylene group is optionally substituted by —O—, —N— or —S—, and the like are used. Here, the position at which —C— of the alkylene group or alkenylene group is substituted by —O—, —N— or —S— may be any position at the terminal or in the chain of the alkylene group or alkenylene group.

As the substituent of the "alkylene group" or "alkenylene group", for example, $C_{1-6}$ alkyl group, oxo group, $C_{6-14}$ aryl group (e.g., phenyl) and the like can be mentioned. The number of the substituents is, for example, 1 to 3.

As the salt of compound (I), a pharmacologically acceptable salt is preferable. As such salt, for example, salts with inorganic base, salts with organic base, salts with inorganic acid, salts with organic acid, salts with basic or acidic amino acid and the like can be mentioned.

Preferable examples of the salt with inorganic base include alkali metal salts such as sodium salt, potassium salt and the like; alkaline earth metal salts such as calcium salt, magnesium salt and the like; aluminum salt; ammonium salts and the like.

Preferable examples of the salt with organic base include a salt with trimethylamine, triethylamine, pyridine, picoline, ethanolamine, diethanolamine, triethanolamine, dicyclohexylamine, N,N-dibenzylethylenediamine and the like.

Preferable examples of the salt with inorganic acid include a salt with hydrochloric acid, hydrobromic acid, nitric acid, sulfuric acid, phosphoric acid and the like.

Preferable examples of the salt with organic acid include a salt with formic acid, acetic acid, trifluoroacetic acid, fumaric acid, oxalic acid, tartaric acid, maleic acid, citric acid, succinic acid, malic acid, methanesulfonic acid, benzenesulfonic acid, p-toluenesulfonic acid and the like.

Preferable examples of the salt with basic amino acid include a salt with arginine, lysine, ornithine and the like.

Preferable examples of the salt with acidic amino acid include a salt with aspartic acid, glutamic acid and the like.

A prodrug of compound (I) is a compound that converts to compound (I) due to the reaction with enzyme, gastric acid and the like under the physiological conditions in the living body; that is, a compound that converts to compound (I) by enzymatic oxidation, reduction, hydrolysis and the like, and a compound that converts to compound (I) by hydrolysis and the like by gastric acid and the like.

Examples of the prodrug of compound (I) include a compound wherein an amino group of compound (I) is acylated, alkylated or phosphorylated (e.g., a compound wherein an amino group of compound (I) is eicosanoylated, alanylated, pentylaminocarbonylated, (5-methyl-2-oxo-1,3-dioxolen-4-yl)methoxycarbonylated, tetrahydrofuranylated, pyrrolidylmethylated, pivaloyloxymethylated, tert-butylated and the like); a compound wherein a hydroxy group of compound (I) is acylated, alkylated, phosphorylated or borated (e.g., a compound wherein a hydroxy group of compound (I) is acetylated, palmitoylated, propanoylated, pivaloylated, succinylated, fumarylated, alanylated, dimethylaminomethylcarbonylated and the like); a compound wherein a carboxyl group of compound (I) is esterified or amidated (e.g., a compound wherein a carboxyl group of compound (I) is ethyl esterified, phenyl esterified, carboxymethyl esterified, dimethylaminomethyl esterified, pivaloyloxymethyl esterified, ethoxycarbonyloxyethyl esterified, phthalidyl esterified, (5-methyl-2-oxo-1,3-dioxolen-4-yl) methyl esterified, cyclohexyloxycarbonylethyl esterified, methylamidated and the like) and the like. Of these, a compound wherein a carboxyl group of compound (I) is esterified by $C_{1-6}$ alkyl group such as methyl, ethyl, tert-butyl and the like is preferable. These compounds can be produced from compound (I) by a method known per se.

A prodrug of compound (I) may be a compound that converts to compound (I) under physiological conditions as described in Development of Pharmaceutical Products, vol. 7, Molecule Design, 163-198, Hirokawa Shoten (1990).

Preferable examples of compound (I) include the following compounds (I-1), (I-2), (I-3) and (I-4).

Compound (I-1)

A compound represented by the formula

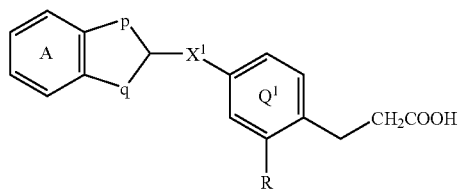

(I-1)

wherein ring A is a benzene ring optionally having substituent(s), ring $Q^1$ is a benzene ring optionally having substituent(s), $X^1$ is a spacer other than an alkylene group, p and q are each independently a bond or a carbon chain having 1 to 4 carbon atoms and optionally having substituent(s), and R is a hydrogen atom or a substituent.

Of compounds (I-1), a compound wherein ring A is a benzene ring optionally having 1 to 3 substituents selected from 1) halogen atom, 2) $C_{1-6}$ alkyl group, 3) $C_{1-6}$ alkoxy group, 4) $C_{6-14}$ aryl group (preferably phenyl) optionally substituted by halogen atom, $C_{1-6}$ alkyl group or $C_{1-6}$ alkoxy group, 5) $C_{6-14}$ aryloxy group (preferably phenoxy), and 6) $C_{7-16}$ aralkyloxy group (preferably benzyloxy, phenylethyloxy, phenylpropyloxy, phenylbutyloxy);

ring $Q^1$ is a benzene ring optionally having 1 to 3 substituents selected from halogen atom and $C_{1-6}$ alkyl group;

$X^1$ is an oxygen atom;

p and q are each independently a bond or $C_{1-4}$ alkylene; and

R is a hydrogen atom, is preferable.

Compound (I-2)

A compound represented by the formula

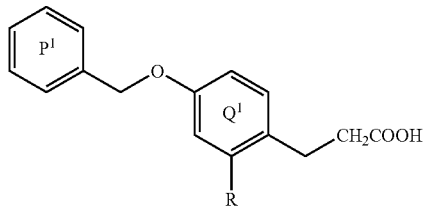

(I-2)

wherein ring $P^1$ is a benzene ring having substituent(s) having a benzene ring, ring $Q^1$ is a benzene ring optionally having substituent(s), and R is a hydrogen atom or a substituent.

Of compounds (I-2), a compound wherein ring $P^1$ is a benzene ring having substituent(s) represented by the formula: $R^1$-$E^1$- ($R^1$ is a phenyl group or an indanyl group, each optionally having substituent(s) selected from halogen atom, nitro group, carboxyl group, optionally halogenated $C_{1-6}$ alkyl group, hydroxy-$C_{1-6}$ alkyl group, carboxy-$C_{1-6}$ alkyl-carbonylamino-$C_{1-6}$ alkyl group, optionally halogenated $C_{1-6}$ alkoxy group, $C_{6-14}$ aryl group, $C_{6-14}$ aryloxy group and $C_{7-16}$ aralkyloxy group, and $E^1$ is a bond or a spacer (preferably —O—, —CH$_2$—O—, —CO—, —CONH—, —N(CH$_3$)CH$_2$—, —S—CH$_2$— or —CH=CH—) and optionally substituted by $C_{1-6}$ alkyl group;

ring $Q^1$ is a benzene ring optionally having $C_{1-6}$ alkyl group; and

R is a hydrogen atom, is preferable.

As compound (I-2), a compound represented by the formula

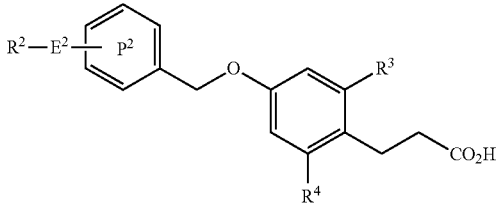

(2)

wherein $R^2$ is a phenyl group having 1 or 2 substituents, $E^2$ is a bond, an oxygen atom or an optionally substituted methylene, ring $P^2$ is a benzene ring optionally further having substituent(s) selected from an optionally substituted $C_{1-6}$ alkyl group, an optionally substituted $C_{1-6}$ alkoxy group and a halogen atom, and $R^3$ and $R^4$ are each independently a hydrogen atom, a halogen atom, a $C_{1-6}$ alkyl group or a $C_{1-6}$ alkoxy group is also preferable.

Of compounds (I-2A), a compound wherein $R^2$ is a phenyl group having 1 or 2 substituents selected from 1) a $C_{1-6}$ alkyl group or a $C_{1-6}$ alkoxy group, each optionally having 1 to 5 substituents selected from halogen atom; hydroxy group; amino group; a 5- to 7-membered heterocyclic group containing, besides a carbon atom, one or two kinds of 1 to 4 hetero atoms selected from a nitrogen atom, a sulfur atom and an oxygen atom (e.g., furyl, pyridyl, thienyl) (the heterocyclic group is optionally substituted by halogen atom, hydroxy group, amino group, optionally halogenated $C_{1-6}$ alkyl group, mono- or di-$C_{1-6}$ alkylamino group, mono- or di-$C_{6-14}$ arylamino group, $C_{3-8}$ cycloalkyl group, $C_{1-6}$ alkoxy group, $C_{1-6}$ alkoxy-carbonyl group, $C_{1-6}$ alkylthio group, $C_{1-6}$ alkylsulfinyl group, $C_{1-6}$ alkylsulfonyl group, optionally esterified carboxyl group, carbamoyl group, thiocarbamoyl group, mono-$C_{1-6}$ alkyl-carbamoyl group, di-$C_{1-6}$ alkyl-carbamoyl group, mono- or di-$C_{6-14}$ aryl-carbamoyl group and the like); mono- or di-$C_{1-6}$ alkylamino group; mono- or di-$C_{6-14}$ arylamino group; $C_{3-8}$ cycloalkyl group; optionally halogenated $C_{1-6}$ alkoxy group; $C_{1-6}$ alkoxy-carbonyl group; $C_{1-6}$ alkylthio group; $C_{1-6}$ alkylsulfinyl group; $C_{1-6}$ alkylsulfonyl group; optionally esterified carboxyl group; carbamoyl group; thiocarbamoyl group; mono-$C_{1-6}$ alkyl-carbamoyl group; di-$C_{1-6}$ alkyl-carbamoyl group; mono- or di-$C_{6-14}$ aryl-carbamoyl group (e.g., phenylcarbamoyl, 1-naphthylcarbamoyl, 2-naphthylcarbamoyl); mono- or di-(5- to 7-membered heterocycle containing, besides a carbon atom, one or two kinds of 1 to 4 hetero atoms selected from a nitrogen atom, a sulfur atom and an oxygen atom)-carbamoyl group (e.g., 2-pyridylcarbamoyl, 3-pyridylcarbamoyl, 4-pyridylcarbamoyl, 2-thienylcarbamoyl, 3-thienylcarbamoyl); $C_{1-6}$ alkyl-carbonylamino group optionally substituted by carboxyl group; and 2) halogen atom;

$E^2$ is a bond, an oxygen atom or methylene;

ring $P^2$ is a benzene ring; and $R^3$ and $R^4$ are each independently a hydrogen atom, a halogen atom, a $C_{1-6}$ alkyl group or a $C_{1-6}$ alkoxy group; is preferable.

Compound (I-3)

A compound represented by the formula

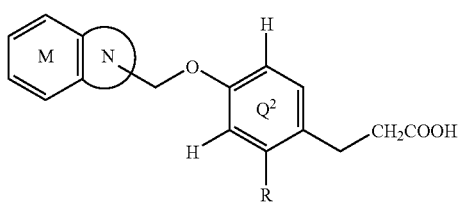

(I-3)

wherein ring M is a benzene ring optionally having substituent(s), ring N is a 5-membered heterocycle optionally having substituent(s), ring $Q^2$ is a benzene ring optionally having substituent(s), and R is a hydrogen atom or a substituent.

Of compounds (I-3), a compound wherein the partial structural formula

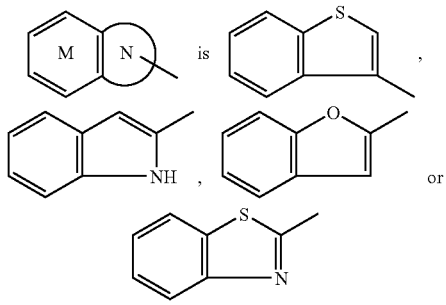

each optionally having substituent(s) selected from a halogen atom and an optionally substituted $C_{1-6}$ alkyl group (preferably, an optionally halogenated $C_{1-6}$ alkyl group), ring $Q^2$ is a benzene ring; and R is a hydrogen atom is preferable.

Compound (I-4)

A compound represented by the formula

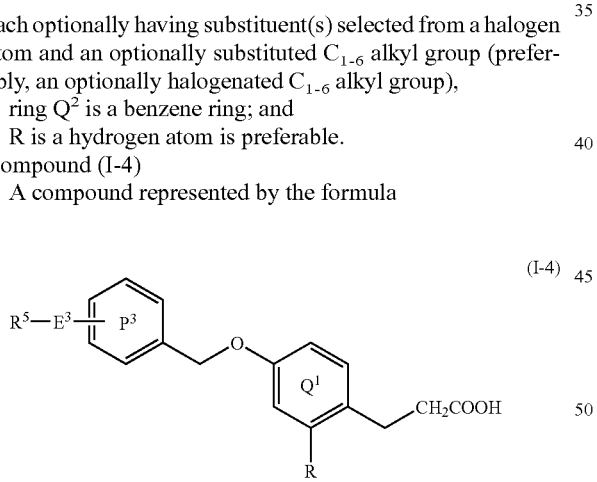

(I-4)

wherein $R^5$ is a thiazolyl group optionally having substituent(s), $E^3$ is a bond or a spacer, ring $P^3$ and ring $Q^1$ are each independently a benzene ring optionally having substituent(s), and R is a hydrogen atom or a substituent.

Of compounds (I-4), a compound wherein $R^5$ is a thiazolyl group (preferably 2-thiazolyl group) optionally having 1 or 2 substituents selected from $C_{6-14}$ aryl group (preferably phenyl) and $C_{1-6}$ alkyl group;

$E^3$ is —N($R^6$)—(CH$_2$)m- or —S—(CH$_2$)m- ($R^6$ is hydrogen atom or $C_{1-6}$ alkyl group, and m is an integer of 0 to 3);

ring $P^3$ and ring $Q^1$ are each a benzene ring; and

R is a hydrogen atom, a halogen atom, a $C_{1-6}$ alkyl group or a $C_{1-6}$ alkoxy group is preferable.

As compound (I-4), a compound represented by the formula

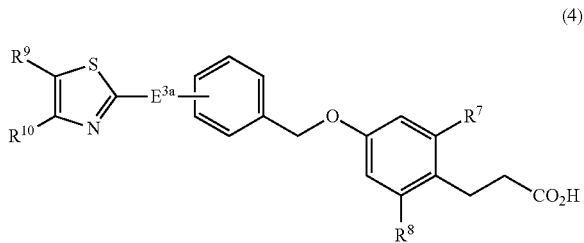

(4)

wherein $E^{3a}$ is —N($R^{11}$)—CH$_2$—, —CH($R^{11}$)—O— or —CH($R^{11}$)—CH$_2$— ($R^{11}$ is hydrogen atom or $C_{1-6}$ alkyl group), $R^7$ and $R^8$ are each independently hydrogen atom, halogen atom, $C_{1-6}$ alkyl group or $C_{1-6}$ alkoxy group, $R^9$ and $R^{10}$ are each independently hydrogen atom, optionally substituted $C_{6-14}$ aryl group (preferably optionally partially saturated $C_{6-14}$ aryl group (preferably phenyl, tetrahydronaphthyl), which optionally has 1 to 3 substituents selected from halogen atom, optionally halogenated $C_{1-6}$ alkyl group, optionally halogenated $C_{1-6}$ alkoxy group and $C_{3-8}$ cycloalkyl group (preferably cyclohexyl)) or optionally substituted $C_{1-6}$ alkyl group (preferably $C_{1-6}$ alkyl group optionally substituted by optionally esterified carboxyl (preferably carboxyl)), or $R^9$ and $R^{10}$ are bonded to form a ring (preferably $C_{3-10}$ cycloalkene optionally condensed with benzene ring (preferably cyclopropene, cyclobutene, cyclopentene, cyclohexene)) is also preferable.

Specific examples of preferable compound (I) include
4-([2',6'-dimethyl-1,1'-biphenyl]-3-ylmethoxy)benzenepropanoic acid;
(R)-4-[(2,3-dihydro-1H-inden-1-yl)oxy]benzenepropanoic acid;
4-[[3-[(2,3-dihydro-1H-inden-1-yl)oxy]phenyl]methoxy] benzenepropanoic acid;
3-[4-[(2',6'-dimethylbiphenyl-3-yl)methoxy]-2-fluorophenyl]propionic acid;
3-[4-[[4-[[4,5-dihydronaphtho[1,2-d][1,3]thiazol-2-yl(propyl)amino]methyl]benzyl]oxy]phenyl]propionic acid;
3-[4-[[4-(2,6-dimethylbenzyl)benzyl]oxy]phenyl]propanoic acid;
3-{4-[(4-{[isopropyl(4-phenyl-1,3-thiazol-2-yl)amino]methyl}benzyl)oxy]phenyl}propanoic acid;
3-(4-((4-(((2-phenoxypropyl)amino)methyl)benzyl)oxy)phenyl)propanoic acid;
3-(4-((4-((dibenzylamino)methyl)benzyl)oxy)phenyl)propanoic acid; and
3-(4-((4-(((2-imidazo[1,5-a]pyridin-3-ylethyl)(phenyl)amino)methyl)benzyl)oxy)phenyl)propanoic acid.

(2) A compound described in WO03/099793, which is represented by the formula:

$$\text{(Aa)}-\text{(Ba)}-X_a-Y_a-X_a^1-Y_a^1-\text{(Ca)}-X_a^2-Y_a^2-(C=O)-R_a$$

(II)

wherein
ring Aa is a ring optionally having 1 to 3 substituents;
ring Ba is a 1,2-azole ring optionally further having 1 to 3 substituents;

Xa, Xa¹ and Xa² are each independently a bond, —O—, —S—, —SO—, —SO₂—, —CO—, —CS—, —CRa¹(ORa²)—, —NRa³—, —CONRa³— or —NRa³CO— (Ra¹ is a hydrogen atom or an optionally substituted hydrocarbon group, Ra² is a hydrogen atom or a hydroxy-protecting group, and Ra³ is a hydrogen atom, an optionally substituted hydrocarbon group or an amino-protecting group);

Ya is a divalent aliphatic hydrocarbon residue having 1 to 20 carbon atoms;

Ya¹ and Ya² are each independently a bond or a divalent aliphatic hydrocarbon residue having 1 to 20 carbon atoms;

ring Ca is a monocyclic aromatic ring optionally further having 1 to 3 substituents;

Ra is —ORa⁴ (Ra⁴ is a hydrogen atom or an optionally substituted hydrocarbon group) or —NRa⁵Ra⁶ (Ra⁵ and Ra⁶ are each independently a hydrogen atom, an optionally substituted hydrocarbon group or an optionally substituted heterocyclic group, or Ra⁵ and Ra⁶ form, together with the adjacent nitrogen atom, an optionally substituted heterocycle) (hereinafter sometimes to be abbreviated as compound (II)), or a salt thereof or a prodrug thereof.

As the salt and prodrug of compound (II), those similar to the salt and prodrug of the aforementioned compound (I) can be mentioned.

Of compounds (II), a compound wherein ring Aa is $C_{6-14}$ aromatic hydrocarbon (preferably benzene), 5- or 6-membered aromatic heterocycle (preferably pyridine, pyrimidine, pyridazine, oxadiazole, thiadiazole) or $C_{3-12}$ alicyclic hydrocarbon (preferably cyclopentane), each optionally having 1 to 3 substituents selected from 1) halogen atom;
2) $C_{1-6}$ alkyl group optionally substituted by 1 to 3 halogen atoms;
3) $C_{6-14}$ aryl group (preferably phenyl);
4) $C_{1-6}$ alkoxy group optionally substituted by 1 to 3 halogen atoms;
5) $C_{1-6}$ alkylthio group optionally substituted by 1 to 3 halogen atoms;
6) nitro group;
7) cyano group;
8) amino group optionally substituted by $C_{2-10}$ alkanoyl group or $C_{1-10}$ alkylsulfonyl group (preferably amino, acetylamino, propionylamino, butyrylamino, isobutyrylamino, methylsulfonylamino); and the like;

ring Ba is pyrazole or isoxazole (preferably pyrazole) each optionally having 1 to 3 (preferably 1 or 2) substituents selected from $C_{1-6}$ alkyl group, $C_{1-6}$ alkoxy group, $C_{7-13}$ aralkyloxy group (preferably benzyloxy), hydroxy group, $C_{6-14}$ aryl group (preferably phenyl), $C_{3-10}$ cycloalkyl group (preferably cyclohexyl) and the like;

Xa, Xa¹ and Xa² are each independently a bond or —O—;

Ya is $C_{1-6}$ alkylene or $C_{2-6}$ alkenylene;

Ya¹ is a bond;

Ya² is a bond, $C_{1-6}$ alkylene or $C_{2-6}$ alkenylene;

ring Ca is benzene or 5- or 6-membered monocyclic aromatic heterocycle (preferably pyrazole), each optionally having 1 to 3 substituents selected from 1) halogen atom;
2) $C_{1-6}$ alkyl group optionally substituted by 1 to 3 halogen atoms;
3) $C_{6-14}$ aryl group (preferably phenyl) optionally substituted by 1 to 3 halogen atoms;
4) $C_{1-6}$ alkoxy group optionally substituted by 1 to 3 halogen atoms;
5) $C_{1-6}$ alkylthio group optionally substituted by 1 to 3 halogen atoms;
6) hydroxy group;
7) $C_{7-13}$ aralkyloxy group (preferably benzyloxy);
8) cyano group;
9) $C_{3-10}$ cycloalkyl group (preferably cyclohexyl); and the like; and Ra is —ORa⁴ (Ra⁴ is preferably hydrogen atom or $C_{1-6}$ alkyl group) is preferable.

Specific examples of preferable compound (II) include
3-[1-phenyl-3-(4-[3-[4-(trifluoromethyl)phenyl]-5-isoxazolyl]butoxy)-1H-pyrazol-5-yl]propionic acid;
2-[3-(3-[3-ethoxy-1-[5-(trifluoromethyl)-2-pyridyl]-1H-pyrazol-4-yl]propoxy)phenoxy]-2-methylpropionic acid;
3-[2-ethoxy-4-(3-[3-ethoxy-1-[5-(trifluoromethyl)-2-pyridyl]-1H-pyrazol-4-yl]propoxy)phenyl]propionic acid;
3-[3-(3-[3-ethoxy-1-[5-(trifluoromethyl)-2-pyridyl]-1H-pyrazol-4-yl]propoxy)-1-phenyl-1H-pyrazol-5-yl]propionic acid;
[1-phenyl-3-(4-{3-propyl-1-[5-(trifluoromethyl)-2-pyridinyl]-1H-pyrazol-4-yl}butoxy)-1H-pyrazol-4-yl]acetic acid;
[2-(3-{3-isopropyl-1-[5-(trifluoromethyl)-2-pyridyl]-1H-pyrazol-4-yl}propoxy)-3-methoxyphenyl]acetic acid;
[2-(3-{3-(1-ethylpropyl)-1-[5-(trifluoromethyl)-2-pyridyl]-1H-pyrazol-4-yl}propoxy)-3-methoxyphenyl]acetic acid;
(2-[3-[1-(5-chloro-2-pyridyl)-3-(1-ethylpropyl)-1H-pyrazol-4-yl]propoxy]-3-methoxyphenyl)acetic acid;
[3-ethyl-2-(3-[3-isopropyl-1-[6-(trifluoromethyl) pyridazin-3-yl]-1H-pyrazol-4-yl]propoxy)phenyl]acetic acid;
[2-(3-{3-isopropyl-1-[6-(trifluoromethyl)pyridazin-3-yl]-1H-pyrazol-4-yl}propoxy)-3-methoxyphenyl]acetic acid;
[3-(3-{3-isopropyl-1-[5-(trifluoromethyl)-2-pyridinyl]-1H-pyrazol-4-yl}propoxy)-1-methyl-1H-pyrazol-4-yl]acetic acid;
[1-ethyl-5-(3-{3-isopropyl-1-[5-(trifluoromethyl)-2-pyridinyl]-1H-pyrazol-4-yl}propoxy)-1H-pyrazol-4-yl]acetic acid;
[1-ethyl-5-(3-{3-propyl-1-[5-(trifluoromethyl)-2-pyridinyl]-1H-pyrazol-4-yl}propoxy)-1H-pyrazol-4-yl]acetic acid;
(2-{3-[1-(5-bromo-2-pyridinyl)-3-(1-ethylpropyl)-1H-pyrazol-4-yl]propoxy}-3-methoxyphenyl)acetic acid; and
[2-(3-{3-tert-butyl-1-[6-(trifluoromethyl)pyridazin-3-yl]-1H-pyrazol-4-yl}propoxy)-3-methylphenyl]acetic acid.

(3) A compound described in WO2004/022551, which is represented by the formula:

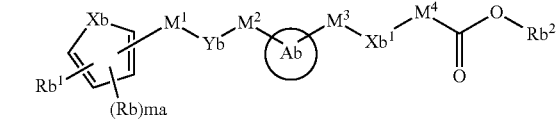

wherein Rb is an optionally substituted hydrocarbon group or an optionally substituted heterocyclic group, ma is 0, 1 or 2, and when ma is 2, each Rb may be the same or different, Rb² is a hydrogen atom or an optionally substituted hydrocarbon group, Rb¹ is an optionally substituted aromatic group, ring Ab is an optionally substituted monocyclic aromatic ring or an optionally substituted bicyclic aromatic fused ring, Xb is an oxygen atom or a sulfur atom, Xb¹ is a bond, an oxygen atom or —S(O)mb- (wherein mb is 0, 1 or 2), Yb is a bond, an oxygen atom, —S(O)mc-, —C(=O)—N(Rb³)— or —N(Rb³)—C(=O)— (Rb³ is a hydrogen atom, an optionally substituted hydrocarbon group or an optionally substituted heterocyclic group, and mc is 0, 1 or 2), M¹, M² and M³ are each independently a bond or an optionally substituted divalent aliphatic hydrocarbon group, and M⁴ is an optionally substituted divalent aliphatic hydrocarbon group,
or a salt thereof or a prodrug thereof.

As the salt and prodrug of compound (III), those similar to the salt and prodrug of the aforementioned compound (I) can be mentioned.

Of compounds (III), a compound wherein Rb is an alkyl group, an aryl group or a cycloalkyl group, each of which is optionally substituted (preferably $C_{1-4}$ alkyl group optionally substituted by 1 to 3 halogen atoms or hydroxy; phenyl group optionally substituted by 1 to 3 halogen atoms; or $C_{3-10}$ cycloalkyl group);
ma is 0 or 1;
$Rb^2$ is a hydrogen atom;
$Rb^1$ is an optionally substituted phenyl group (preferably phenyl group optionally having 1 to 3 substituents selected from 1) halogen atom; 2) $C_{1-6}$ alkyl group optionally substituted by 1 to 3 halogen atoms; and 3) $C_{1-6}$ alkoxy group optionally substituted by 1 to 3 halogen atoms);
ring Ab is a benzene ring or a thiazole ring, each of which is optionally substituted (preferably benzene ring or thiazole ring, each optionally having 1 or 2 substituents selected from $C_{1-6}$ alkyl and $C_{1-6}$ alkoxy);
Xb is an oxygen atom;
$Xb^1$ is a bond, an oxygen atom or —S(O)mb- (mb is 0, 1 or 2);
Yb is an oxygen atom or —C(=O)—N($Rb^3$)— ($Rb^3$ is hydrogen atom, alkyl group (preferably $C_{1-10}$ alkyl group) or aralkyl group (preferably $C_{7-13}$ aralkyl group), the carbon atom is bonded to $M^1$ and the nitrogen atom is bonded to $M^2$);
$M^1$, $M^2$ and $M^3$ are each independently a bond or alkylene (preferably $C_{1-6}$ alkylene); and
$M^4$ is alkylene (preferably $C_{1-6}$ alkylene) is preferable.

(4) The following fatty acids described in WO02/057783 as GPR40 ligands.

Saturated or unsaturated $C_{6-23}$ fatty acids selected from trans-retinoic acid, cis-4,7,10,13,16,19-docosahexaenoic acid, palmitic acid, pentadecanoic acid, elaidic acid, petroselinic acid, heptadecanoic acid, tridecanoic acid, lauric acid, arachidonic acid, linolenic acid, palmitoleic acid, capric acid, myristic acid, stearic acid, undecanoic acid and the like.

(5) A compound obtained by the "screening method for GPR40 agonist" described in WO02/057783, WO2004/041266 and the like.

(6) A compound described in WO2004/106276, which is represented by the formula:

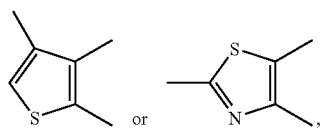
(IV)

wherein Ar is an optionally substituted cyclic group, ring Ac is a ring optionally further substituted (provided that the ring is not thiazole, oxazole, imidazole and pyrazole),
Xe and Xf are each independently a bond or a spacer having a main chain of 1 to 5 atoms,
Xc is O, S, SO or $SO_2$,

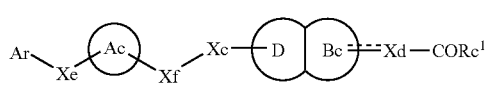

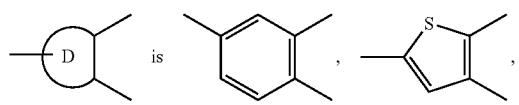

ring Bc is a 5- to 7-membered ring,
Xd is a bond, CH or $CH_2$,
⋯⋯ is a single bond when Xd is a bond or $CH_2$, or a double bond when Xd is CH, and
$Rc^1$ is an optionally substituted hydroxy group, provided that
(i) when ring Ac is benzene, the cyclic group represented by Ar is not a quinolinyl group,
(ii) when ring Bc is a 5- to 7-membered aromatic ring, the ring represented by ring Ac is not thiophene and furan,
(iii) when ring Bc is benzene, the ring represented by ring Ac is not a 5-membered aromatic heterocycle, and
(iv) when ring Bc is cyclohexane, Xd is not a bond, or a salt thereof or a prodrug thereof.

As the salt and prodrug of compound (IV), those similar to the salt and prodrug of the aforementioned compound (I) can be mentioned.

Of compounds (IV), a compound wherein
Ar is an aromatic hydrocarbon group (preferably $C_{6-14}$ aryl group; more preferably phenyl) optionally having 1 to 3 substituents selected from halogen atom; cyano group; optionally halogenated $C_{1-6}$ alkyl group; $C_{6-14}$ aryl group; hydroxy group; $C_{1-10}$ alkoxy group optionally substituted by 1 to 3 substituents selected from $C_{3-8}$ cycloalkyl group, optionally halogenated $C_{1-6}$ alkoxy group and the like; heterocyclyloxy group (preferably tetrahydropyranyloxy); $C_{7-16}$ aralkyloxy group; carboxyl group; $C_{1-6}$ alkyl-carbonyl group; $C_{6-14}$ aryl-carbonyl group; and the like;
ring Ac is an aromatic ring (preferably benzene, furan, thiophene, oxadiazole, triazole, tetrazole, pyrimidine, benzimidazole, indole) optionally having 1 to 3 substituents selected from halogen atom, $C_{7-16}$ aralkyl group, $C_{6-14}$ aryl group, $C_{1-10}$ alkoxy group, $C_{7-16}$ aralkyloxy group and the like;
Xe is a bond; —O—; —S—; —$CH_2$—; —CO—; —$CH_2O$—; —$CH_2S$—; —$CH_2NH$— optionally having, on the N atom, a substituent selected from $C_{1-6}$ alkyl group and $C_{7-16}$ aralkyl group; —$OCH_2$—; —$SCH_2$—; —NH—$CH_2$— optionally having, on the N atom, a substituent selected from $C_{1-6}$ alkyl group and $C_{7-16}$ aralkyl group; —$CH_2CH_2O$—; —$CH_2CH_2S$—; or —$CH_2$—NH—CO— optionally having, on the N atom, a substituent selected from $C_{1-6}$ alkyl group and $C_{7-16}$ aralkyl group;
Xf is —$CH_2$—; —$CH_2CH_2$—; —CO—$CH_2$—; —$CH_2CH_2CH_2$—; —O—$CH_2CH_2$—; —S—$CH_2CH_2$—; —O—$CH_2CH_2CH_2$—; —S—$CH_2CH_2CH_2$—; or —NH—$CH_2CH_2$— or —$CH_2$—NH—$CH_2CH_2$— each optionally having, on the N atom, a substituent selected from $C_{3-8}$ cycloalkyl group and $C_{7-16}$ aralkyl group;

Xc is O;

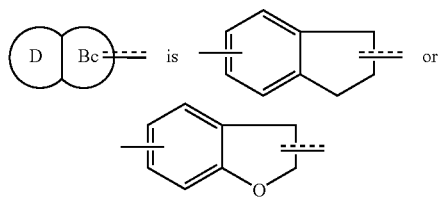

Xd is CH₂; and
Rc¹ is hydroxy group or $C_{1-6}$ alkoxy group is preferable.
Preferable examples of compound (IV) include the following compounds (IV-1) and (IV-2).

Compound (IV-1)
A compound represented by the formula

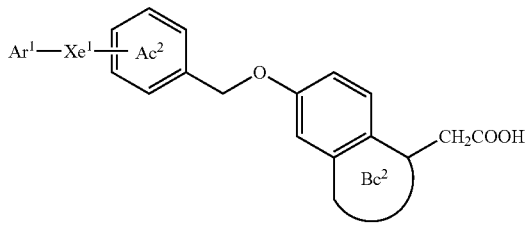

wherein Ar¹ is an optionally substituted phenyl group or an optionally substituted indanyl group,
Xe¹ is a bond or a spacer having a main chain of 1 to 5 atoms,
ring Ac² is a benzene ring optionally further substituted, and
ring Bc² is a 5- to 7-membered ring.

Here, Ar¹ is preferably a phenyl group or an indanyl group, each optionally having substituent(s) selected from halogen atom, nitro group, carboxyl group, optionally halogenated $C_{1-6}$ alkyl group, hydroxy-$C_{1-6}$ alkyl group, carboxy-$C_{1-6}$ alkylcarbonylamino-$C_{1-6}$ alkyl group, optionally halogenated $C_{1-6}$ alkoxy group, $C_{6-14}$ aryl group, $C_{6-14}$ aryloxy group and $C_{7-16}$ aralkyloxy group.

Xe¹ is preferably a bond, —O—, —CH₂—O—, —CO—, —CONH—, —N(CH₃)CH₂—, —S—CH₂— or —CH═CH—.

Ring Ac² is preferably a benzene ring optionally further substituted by $C_{1-6}$ alkyl group.

In the formula (IV-1) and the below-mentioned formula (IV-2),

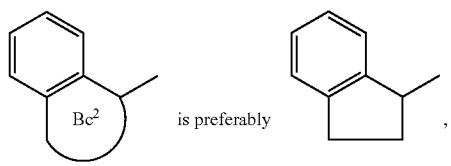 is preferably

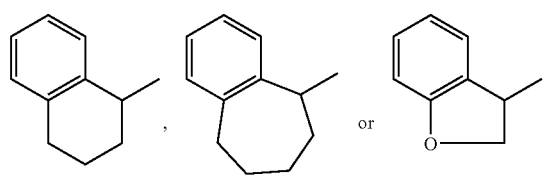

Compound (IV-2)
A compound represented by the formula

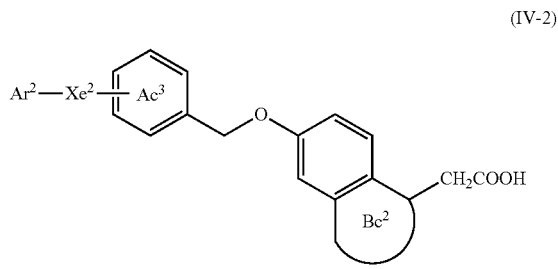

wherein Ar² is an optionally substituted thiazolyl group, Xe² is a bond or a spacer having a main chain of 1 to 5 atoms,
ring Ac³ is a benzene ring optionally further substituted, and
ring Bc² is a 5- to 7-membered ring.

Here, Ar² is preferably a thiazolyl group optionally having substituent(s) selected from $C_{6-14}$ aryl group and $C_{1-6}$ alkyl group.

Xe² is preferably —N(R¹²)—(CH₂)md- or —S—(CH₂)md- (R¹² is hydrogen atom or $C_{1-6}$ alkyl group, and md is an integer of 0 to 3).

Ring Ac³ is preferably a benzene ring.

Specific examples of preferable compound (IV) include
{6-[(2',6'-dimethylbiphenyl-3-yl)methoxy]-1,2,3,4-tetrahydronaphthalen-1-yl}acetic acid;
8-[(2',6'-dimethylbiphenyl-3-yl)methoxy]-2,3,4,5-tetrahydro-1-benzoxepine-4-carboxylic acid;
{5-[(2',6'-dimethylbiphenyl-3-yl)methoxy]-2,3-dihydro-1H-inden-1-yl}acetic acid;
{6-[(2',6'-dimethylbiphenyl-3-yl)methoxy]-2,3-dihydro-1-benzofuran-3-yl}acetic acid;
(6-{[3-(2-methyl-1-naphthyl)benzyl]oxy}-2,3-dihydro-1-benzofuran-3-yl)acetic acid;
[6-({4-[(2-phenyl-1H-indol-1-yl)methyl]benzyl}oxy)-2,3-dihydro-1-benzofuran-3-yl]acetic acid;
(6-{[4'-(benzyloxy)-2',6'-dimethylbiphenyl-3-yl]methoxy}-2,3-dihydro-1-benzofuran-3-yl)acetic acid;
(6-{[4'-(2-ethoxyethoxy)-2',6'-dimethylbiphenyl-3-yl]methoxy}-2,3-dihydro-1-benzofuran-3-yl)acetic acid;
calcium (6-{[4'-(2-ethoxyethoxy)-2',6'-dimethylbiphenyl-3-yl]methoxy}-2,3-dihydro-1-benzofuran-3-yl)acetate; and
(6-{[6-(benzyloxy)-2',6'-dimethylbiphenyl-3-yl]methoxy}-2,3-dihydro-1-benzofuran-3-yl)acetic acid.

(7) A compound described in WO2005/051890, which is represented by the formula:

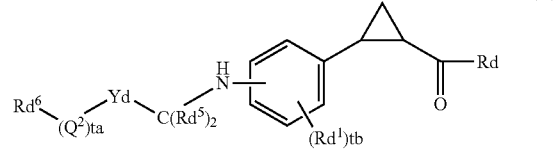

wherein tb is 0, 1, 2, 3 or 4;
Rd¹ is alkyl, alkoxy, halogen, haloalkyl, nitro, cyano or —NRd⁷Rd⁸ (Rd⁷ and Rd⁸ are each independently H or alkyl);
Rd is —OH or —NRd²Rd³ (Rd² and Rd³ are each independently H or -(Q¹)tc-Rd⁴ (tc is 0, 1 or 2; Q¹ is alkylene; and Rd⁴ is alkyl, haloalkyl, aryl, heteroaryl, heterocyclyl, hydroxy, alkoxy or aryloxy));

each $Rd^5$ is independently H or alkyl;
Yd is aryl or heteroaryl, each optionally substituted;
ta is 0 or 1;
$Q^2$ is —$NRd^5$—, —O—, —S—, —O(CH$_2$)td- or —CH$_2$— (td is 1, 2 or 3); and
$Rd^6$ is aryl or heteroaryl, each optionally substituted, or a salt thereof or a prodrug thereof.

As the salt and prodrug of compound (V), those similar to the salt and prodrug of the aforementioned compound (I) can be mentioned.

Of compounds (V), a compound wherein tb is 0; Rd is —OH; $Rd^5$ is H; Yd is phenyl optionally substituted by $C_{1-6}$ alkyl, $C_{1-6}$ alkoxy, halogen or $C_{1-6}$ haloalkyl; or Yd is thiazolyl optionally substituted by $C_{1-6}$ alkyl, aryl or heteroaryl; ta is 0 or 1 (preferably 1); $Q^2$ is —O—; and $Rd^6$ is phenyl optionally substituted by halogen, $C_{1-6}$ alkyl, $C_{1-6}$ alkoxy or $C_{1-6}$ haloalkyl is preferable.

As the therapeutic agent for diabetes with sulfonylurea secondary failure of the present invention, a GPR40 agonist can be administered as it is or as a pharmaceutical composition after admixing with a pharmacologically acceptable carrier and the like, to a mammal (e.g., human, mouse, rat, rabbit, dog, cat, bovine, horse, swine, monkey).

While the content of the GPR40 agonist in the agent of the present invention varies depending on the kind of the GPR40 agonist, the size of the preparation and the like, it is, for example, 1 to 90 wt %, preferably 5 to 80 wt %.

Various organic or inorganic carriers conventionally used as materials for pharmaceutical preparations are used as the aforementioned pharmacologically acceptable carrier, which are added as excipient, lubricant, binder and disintegrant for solid preparations; and solvent, dissolution aids, suspending agent, isotonicity agent, buffer and soothing agent and the like for liquid preparations. Where necessary, preparation additive such as preservative, antioxidant, coloring agent, sweetening agent and the like can be used.

Preferable examples of the excipient include lactose, sucrose, D-mannitol, D-sorbitol, starch, pregelatinized starch, dextrin, crystalline cellulose, low-substituted hydroxypropylcellulose, carboxymethylcellulose sodium, gum arabic, pullulan, light anhydrous silicic acid, synthetic aluminum silicate, magnesium aluminometasilicate and the like.

Preferable examples of the lubricant include magnesium stearate, calcium stearate, talc, colloidal silica and the like.

Preferable examples of the binder include pregelatinized starch, saccharose, gelatin, gum arabic, methylcellulose, carboxymethylcellulose, carboxymethylcellulose sodium, crystalline cellulose, sucrose, D-mannitol, trehalose, dextrin, pullulan, hydroxypropylcellulose, hydroxypropylmethylcellulose, polyvinylpyrrolidone and the like.

Preferable examples of the disintegrant include lactose, sucrose, starch, carboxymethylcellulose, carboxymethylcellulose calcium, croscarmellose sodium, carboxymethylstarch sodium, light anhydrous silicic acid, low-substituted hydroxypropylcellulose and the like.

Preferable examples of the solvent include water for injection, physiological saline, Ringer's solution, alcohol, propylene glycol, polyethylene glycol, sesame oil, corn oil, olive oil, cottonseed oil and the like.

Preferable examples of the dissolution aids include polyethylene glycol, propylene glycol, D-mannitol, trehalose, benzyl benzoate, ethanol, trisaminomethane, cholesterol, triethanolamine, sodium carbonate, sodium citrate, sodium salicylate, sodium acetate and the like.

Preferable examples of the suspending agent include surfactants such as stearyltriethanolamine, sodium lauryl sulfate, lauryl aminopropionate, lecithin, benzalkonium chloride, benzethonium chloride, glycerol monostearate and the like; for example, hydrophilic polymers such as polyvinyl alcohol, polyvinylpyrrolidone, carboxymethylcellulose sodium, methylcellulose, hydroxymethylcellulose, hydroxyethylcellulose, hydroxypropylcellulose and the like; polysorbates, polyoxyethylene hydrogenated castor oil and the like.

Preferable examples of an isotonicity agent include sodium chloride, glycerin, D-mannitol, D-sorbitol, glucose and the like.

Preferable examples of the buffer include buffers such as phosphate, acetate, carbonate, citrate and the like, and the like.

Preferable examples of the soothing agent include benzyl alcohol and the like.

Preferable examples of the preservative include p-hydroxybenzoic acid esters, chlorobutanol, benzyl alcohol, phenethyl alcohol, dehydroacetic acid, sorbic acid and the like.

Preferable examples of the antioxidant include sulfite, ascorbate and the like.

Preferable examples of the coloring agent include water-soluble edible tar pigments (e.g., food colors such as Food Color Red Nos. 2 and 3, Food Color Yellow Nos. 4 and 5, Food Color Blue Nos. 1 and 2 and the like), water-insoluble lake pigments (e.g., aluminum salt of the aforementioned water-soluble edible tar pigment), natural pigments (e.g., β-carotene, chlorophil, red iron oxide, yellow iron sesquioxide) and the like.

Preferable examples of the sweetening agent include saccharin sodium, dipotassium glycyrrhizinate, aspartame, stevia and the like.

Examples of the dosage form of the agent of the present invention include oral agents such as tablets (inclusive of sublingual tablets and orally disintegrable tablets), capsules (inclusive of soft capsules and micro capsules), granules, powders, troches, syrups, emulsions, suspensions and the like; and a parenteral agent such as injections (e.g., subcutaneous injections, intravenous injections, intramuscular injections, intraperitoneal injections etc.), external agents (e.g., preparations for nasal administration, transdermal preparations, ointments etc.), suppositories (e.g., rectal suppositories, vaginal suppositories etc.), pellets, drip infusion, eye drop, pulmonary preparations (inhalants) and the like, each of which can be safely administered orally or parenterally. In addition, these preparations may also be controlled-release preparations such as rapid-release preparations and sustained-release preparations (e.g., sustained-release microcapsules etc.). Of these preparations, oral preparations superior in convenience or compliance are preferable.

The agent of the present invention can be produced by a conventional method in the technical field of formulation of preparations, for example, the method described in the Japan Pharmacopoeia and the like.

In the present specification, the "sulfonylurea secondary failure" of the "diabetes with sulfonylurea secondary failure" means the condition where a sufficient hypoglycemic effect cannot be afforded when a pharmaceutical agent (e.g., sulfonylurea compound, fast-acting insulin secretagogue) that stimulates insulin secretion from pancreatic β cells by binding to sulfonylurea receptor 1 (SUR1) which is a part of the ATP-sensitive K$^+$ channel (hereinafter sometimes to be abbreviated as $K_{ATP}$ channel) located at the membrane of pancreatic β cells, closing the $K_{ATP}$ channel, thus depolarizing the cellular membrane, is administered repeatedly or for a long time (e.g., 2 or mo more weeks, preferably 4 or more weeks).

As the above-mentioned sulfonylurea compound, a compound having a sulfonylurea structure or a derivative thereof (e.g., tolbutamide, glibenclamide, gliclazide, chlorpropamide, tolazamide, acetohexamide, glyclopyramide, glimepiride, glipizide, glybuzole and the like) can be mentioned.

As the fast-acting insulin secretagogue, a compound that promotes insulin secretion from pancreatic β cell in the same manner as a sulfonylurea compound, though it does not have a sulfonylurea structure, such as glinide compounds (e.g., repaglinide, senaglinide, nateglinide, mitiglinide or a calcium salt hydrate thereof etc.), and the like, can be mentioned.

The sulfonylurea secondary failure may be caused by any of a sulfonylurea compound and a fast-acting insulin secretagogue.

As the diabetes of the "diabetes with sulfonylurea secondary failure", for example, type 1 diabetes, type 2 diabetes, gestational diabetes, IGT (Impaired Glucose Tolerance), IFG (Impaired Fasting Glucose), IFG (Impaired Fasting Glycemia), diabetic complications [e.g., neuropathy, nephropathy, retinopathy, cataract, macroangiopathy, osteopenia, hyperosmolar diabetic coma, infections (e.g., respiratory infection, urinary tract infection, gastrointestinal infection, dermal soft tissue infection, inferior limb infection), diabetic gangrene, xerostomia, hypacusis, cerebrovascular disorder, peripheral blood circulation disorder] and the like can be mentioned. Of these, type 2 diabetes is preferable.

Furthermore, diabetes means a disease determined according to the diagnostic criteria of the Japan Diabetes Society, ADA (American Diabetes Association) and WHO, which is "a condition showing any of a fasting blood glucose level (glucose concentration of intravenous plasma) of not less than 126 mg/dl, a 75 g oral glucose tolerance test (75 g OGTT) 2 h level (glucose concentration of intravenous plasma) of not less than 200 mg/dl, and a non-fasting blood glucose level (glucose concentration of intravenous plasma) of not less than 200 mg/dl".

In the present specification, "diabetes with sulfonylurea secondary failure" preferably means a "condition in which a non-fasting blood glucose level of less than 200 mg/dl and a blood glucose level during fasting (deprived of food for at least 8 hr) of less than 126 mg/dl are retained after administration of a sulfonylurea compound or a fast-acting insulin secretagogue, thereafter a non-fasting blood glucose level of not less than 200 mg/dl or a fasting blood glucose level of not less than 126 mg/dl occurs even when a sulfonylurea compound or a fast-acting insulin secretagogue is administered at the maximum dose".

The therapeutic agent for diabetes with sulfonylurea secondary failure of the present invention provides a superior insulin secretion effect and a superior hypoglycemic effect even in diabetic patients for whom a sulfonylurea compound or a fast-acting insulin secretagogue fails to provide an insulin secretion effect and therefore, fails to provide a sufficient hypoglycemic effect.

While the dose of the agent of the present invention varies depending on the administration subject, administration route, target disease and the like, for example, for oral administration to adult diabetic patients, the active ingredient, GPR40 agonist, is administered generally at a single dose of about 0.01 to 100 mg/kg body weight, preferably 0.05 to 30 mg/kg body weight, more preferably 0.1 to 10 mg/kg body weight, which dose is desirably administered once or twice a day.

The agent of the present invention can be used in combination with a pharmaceutical agent such as a therapeutic agent for diabetes, a therapeutic agent for diabetic complications, an antihyperlipemia agent, an antihypertensive agent, an antiobestic agent, a diuretic agent, an antithrombotic agent and the like (hereinafter to be abbreviated as a concomitant drug). In this case, the timing of the administration of the agent of the present invention and the concomitant drug is not limited, and they may be administered simultaneously or in a staggered manner to the administration subject. Moreover, the agent of the present invention and a concomitant drug may be administered as two kinds of preparations containing each active ingredient, or as a single preparation containing both active ingredients.

The dose of the concomitant drug can be appropriately selected based on the clinically employed dose as a standard. The mixing ratio of the agent of the present invention and the concomitant drug can be appropriately determined according to the administration subject, administration route, target disease, condition, combination and the like. For example, when the administration subject is a human, 0.01 to 100 parts by weight of a concomitant drug can be used per 1 part by weight of the GPR40 agonist, which is the active ingredient of the agent of the present invention.

As the aforementioned therapeutic agent for diabetes, for example, insulin preparations (e.g., animal insulin preparations extracted from the pancreas of bovine or swine; human insulin preparations genetically synthesized using *Escherichia coli* or yeast; zinc insulin; protamine zinc insulin; fragment or derivative of insulin (e.g., INS-1 etc.)), insulin sensitizers (e.g., Pioglitazone or a salt thereof (preferably hydrochloride), Rosiglitazone or a salt thereof (preferably maleate), Reglixane (JTT-501), Netoglitazone (MCC-555), Rivoglitazone (CS-011), FK-614, Ragaglitazar (NN-622), Tesaglitazar (AZ-242), Muraglitazar (BMS-298585), EML-16336, compounds described in WO99/58510 (e.g., (E)-4-[4-(5-methyl-2-phenyl-4-oxazolylmethoxy)benzyloxyimino]-4-phenylbutyric acid), compounds described in WO01/38325, Edaglitazone (BM-13-1258), MBX-102, Naveglitazar (LY-519818), MX-6054, LY-510929, Balaglitazone (NN-2344), T-131 or a salt thereof, THR-0921 etc.), PPARγ agonist, PPARγ antagonist, PPARγ/α dualagonist, α-glucosidase inhibitors (e.g., voglibose, acarbose, miglitol, emiglitate), biguanides (e.g., phenformin, metformin, buformin or salts thereof (e.g., hydrochloride, fumarate, succinate), GLP-1 receptor agonists [e.g., GLP-1, NN-2211, AC-2993 (exendin-4), BIM-51077 and Aib(8,35)hGLP-1(7,37)NH$_2$], amylin agonists (e.g., pramlintide), phosphotyrosine phosphatase inhibitors (e.g., sodium vanadate), dipeptidyl peptidase IV inhibitors (e.g., NVP-DPP-278, PT-100, P32/98, Vildagliptin (LAF-237), P93/01, TS-021, MK-0431, Saxagliptin (BMS-477118) etc.), β3 agonists (e.g., CL-316243, SR-58611-A, UL-TG-307, SB-226552, AJ-9677, BMS-196085 and AZ40140), gluconeogenesis inhibitors (e.g., glycogen phosphorylase inhibitors, glucose-6-phosphatase inhibitors, glucagon antagonists, somatostatin receptor agonists), SGLT (sodium-glucose cotransporter) inhibitors (e.g., T-1095), 11β-hydroxysteroid dehydrogenase inhibitors (e.g., BVT-3498 etc.), adiponectin or agonists thereof, IKK inhibitors (e.g., AS-2868 etc.), leptin resistance improving drugs, somatostatin receptor agonists (compounds described in WO01/25228, WO03/42204, WO98/44921, WO98/45285, WO99/22735 etc.), glucokinase activators (e.g., Ro-28-1675), JNK inhibitors, GSK3β inhibitors and the like can be mentioned.

Examples of the therapeutic agent for diabetic complications include aldose reductase inhibitors (e.g., Tolrestat, Epalrestat, Zenarestat, Zopolrestat, Minalrestat, Fidarestat, CT-112), neurotrophic factors and increasing drugs thereof (e.g., NGF, NT-3, BDNF, neurotrophin production-secretion promoters described in WO01/14372 (e.g., 4-(4-chlorophenyl)-2-(2-methyl-1-imidazolyl)-5-[3-(2-methylphenoxy) propyl]oxazole etc.)), neuranagenesis stimulators (e.g., Y-128), PKC inhibitors (e.g., ruboxistaurin mesylate; LY-333531), AGE inhibitors (e.g., ALT-946, pimagedine, pyratoxanthine, N-phenacylthiazolium bromide (ALT-766) and EXO-226), active oxygen scavengers (e.g., thioctic acid), cerebral vasodilators (e.g., tiapride, mexiletine), somatostatin receptor agonists (e.g., BIM23190) and apoptosis signal regulating kinase-1 (ASK-1) inhibitors.

Examples of the antihyperlipemia agent include statin compounds that are cholesterol synthesis inhibitors (e.g., pravastatin, simvastatin, lovastatin, atorvastatin, fluvastatin, rosuvastatin, pitavastatin and salts thereof (e.g., sodium salt and calcium salt)), squalene synthase inhibitors (e.g., compounds described in WO97/10224, such as N-[[(3R,5S)-1-(3-acetoxy-2,2-dimethylpropyl)-7-chloro-5-(2,3-dimethoxyphenyl)-2-oxo-1,2,3,5-tetrahydro-4,1-benzoxazepin-3-yl] acetyl]-piperidine-4-acetic acid etc.), fibrate compounds (e.g., bezafibrate, clofibrate, simfibrate and clinofibrate), ACAT inhibitor (e.g., Avasimibe and Eflucimibe), anion exchange resins (e.g., cholestyramine), probucol, nicotinic acid drugs (e.g., nicomol and niceritrol), ethyl icosapentate, phytosterols (e.g., soysterol and γ-oryzanol) and the like.

Examples of the antihypertensive agent include angiotensin converting enzyme inhibitors (e.g., captopril, enalapril, delapril), angiotensin II antagonists (e.g., candesartan cilexetil, losartan, eprosartan, valsartan, telmisartan, irbesartan, tasosartan, 1-[[2'-(2,5-dihydro-5-oxo-4H-1,2,4-oxadiazol-3-yl)biphenyl-4-yl]methyl]-2-ethoxy-1H-benzimidazole-7-carboxylic acid etc.), calcium antagonists (e.g., manidipine, nifedipine, amlodipine, efonidipine, nicardipine), potassium channel openers (e.g., levcromakalim, L-27152, AL 0671 and NIP-121), Clonidine and the like.

Examples of the antiobestic agent include antiobestic agents acting on the central nervous system (e.g., Dexfenfluramine, fenfluramine, phentermine, Sibutramine, amfepramone, dexamphetamine, Mazindol, phenylpropanolamine, clobenzorex; MCH receptor antagonists (e.g., SB-568849; SNAP-7941; compounds included in WO01/82925 and WO01/87834 etc.); neuropeptide Y antagonists (e.g., CP-422935 etc.); cannabinoid receptor antagonists (e.g., SR-141716, SR-147778 etc.); ghrelin antagonist; 11β-hydroxysteroid dehydrogenase inhibitors (e.g., BVT-3498 etc.) and the like), pancreatic lipase inhibitors (e.g., orlistat and ATL-962), β3 agonists (e.g., CL-316243, SR-58611-A, UL-TG-307, SB-226552, AJ-9677, BMS-196085 and AZ40140), peptidic anorexiants (e.g., leptin and CNTF (Ciliary Neurotrophic Factor)), cholecystokinin agonists (e.g., lintitript and FPL-15849) and the like.

Examples of the diuretic agent include xanthine derivatives (e.g., theobromine and sodium salicylate, theobromine and calcium salicylate), thiazide preparations (e.g., ethiazide, cyclopenthiazide, trichloromethiazide, hydrochlorothiazide, hydroflumethiazide, benzylhydrochlorothiazide, penflutizide, polythiazide and methyclothiazide), antialdosterone preparations (e.g., spironolactone and triamterene), carbonate dehydratase inhibitors (e.g., acetazolamide), chlorobenzenesulfonamide preparations (e.g., chlortalidone, mefruside and indapamide), azosemide, isosorbide, etacrynic acid, piretanide, bumetanide, furosemide and the like.

Examples of the antithrombotic agent include heparin (e.g., heparin sodium, heparin calcium and dalteparin sodium), warfarin (e.g., warfarin potassium), anti-thrombin drugs (e.g., aragatroban), thrombolytic agents (e.g., urokinase, tisokinase, alteplase, nateplase, monteplase, pamiteplase), platelet aggregation inhibitors (e.g., ticlopidine hydrochloride, cilostazol, ethyl icosapentate, beraprost sodium and sarpogrelate hydrochloride) and the like.

Preferable concomitant drugs are insulin preparations, insulin sensitizers, α-glucosidase inhibitors, biguanides and the like.

The present invention further relates to "a closing agent of ATP-sensitive $K^+$ channel incapable of closing due to stimuli of sulfonylurea receptor 1-binding compounds (e.g., sulfonylurea compound, fast-acting insulin secretagogue), which comprises a GPR40 agonist".

Here, as the GPR40 agonist, sulfonylurea compound and fast-acting insulin secretagogue, those similar to the aforementioned can be mentioned.

The above-mentioned closing agent can be produced using a GPR40 agonist and used in the same manner as the aforementioned therapeutic agent for diabetes with sulfonylurea secondary failure. Specifically, the closing agent is useful as a therapeutic agent for diabetes with sulfonylurea secondary failure.

The present invention is further explained in detail by referring to the following Example and Experimental Example, which are not to be construed as limitative and may be changed without departing from the scope of the present invention.

In the following Example and Experimental Example, 4-([2',6'-dimethyl-1,1'-biphenyl]-3-ylmethoxy)benzenepropanoic acid is abbreviated as Compound A.

EXAMPLE 1

Compound A (150 mg), lactose (1184 mg), cornstarch (360 mg), HPC-L (trade name, manufactured by Nippon Soda Co., Ltd.) (60 mg), carboxymethylcellulose calcium (trade name: ECG505, manufactured by Gotoku Chemical Company Ltd.) (60 mg), crystalline cellulose (trade name: Avicel, manufactured by Asahi Kasei Corporation) (172 mg) and magnesium stearate (14 mg) are admixed in a mortar. From the obtained mixture, 200 mg is tableted using a hydraulic pump press (manufactured by Riken Seiki Co., Ltd.) to give 8 mm diameter tablets.

EXPERIMENTAL EXAMPLE 1

Preparation Method of N-STZ-1.5 Rat

Streptozocin (STZ) (120 mg/kg body weight) was administered to a 1.5-day-old male WKY rat to prepare a type 2 diabetes model N-STZ-1.5 rat.

Glibenclamide (10 mg/kg body weight/day) was orally administered to the N-STZ-1.5 rats (male, 18 rats) every day for 4 consecutive weeks. After drug cessation for 1 week, glibenclamide (10 mg/kg body weight/day) was orally administered every day for 2 consecutive weeks to give a model of type 2 diabetes with sulfonylurea secondary failure. The rats were divided into 3 groups of Groups A to C (6 rats per group), 0.5% methylcellulose suspension was orally administered to Group A (control group), glibenclamide (10 mg/kg body weight) was orally administered to Group B and Compound A (10 mg/kg body weight) was orally administered to Group C.

At 30 min after the administration, 1 g/kg body weight of a glucose solution was orally administered to each rat, and blood samples were collected from the rat tail vein before administration of the glucose solution and at 10, 30, 60 and 120 minutes after administration of the glucose solution, and the plasma glucose level and plasma insulin level were measured.

The plasma glucose level was measured using an L type Wako Glu2 (trade name, Wako Pure Chemical Industries, Ltd.) according to an enzyme method, and the plasma insulin level was measured using a SHIONORIA insulin kit (trade name, Shionogi & Co., Ltd.) by a radioimmunoassay.

The increment of plasma glucose level at 60 minutes after the glucose solution administration (0 to 60 minutes after glucose loading) and the increment of plasma insulin level at 10 minutes after the glucose solution administration (0 to 10 minutes after glucose loading) are shown in Table 1 and Table 2, respectively. In the Tables, the values show mean values (n=6).

TABLE 1

| Group | Increment of plasma glucose level (mg/dl) |
|---|---|
| Group A (control) | 181.65 |
| Group B (glibenclamide) | 178.40 |
| Group C (Compound A) | 107.12 |

TABLE 2

| Group | Increment of plasma insulin level (μU/ml) |
|---|---|
| Group A (control) | 25.58 |
| Group B (glibenclamide) | 29.37 |
| Group C (Compound A) | 42.76 |

As shown in Table 1, administration of glibenclamide (sulfonylurea compound) to type 2 diabetic rats with sulfonylurea secondary failure failed to show a plasma glucose level lowering effect. However, administration of compound A (GPR40 agonist) exhibited a superior plasma glucose level lowering effect.

As shown in Table 2, moreover, administration of glibenclamide (sulfonylurea compound) to type 2 diabetic rats with sulfonylurea secondary failure hardly showed a plasma insulin level increasing effect. However, administration of Compound A (GPR40 agonist) resulted in a superior plasma insulin level increasing effect.

INDUSTRIAL APPLICABILITY

The therapeutic agent for diabetes with sulfonylurea secondary failure of the present invention provides a superior insulin secretion effect and a superior hypoglycemic effect even in diabetic patients for whom a sulfonylurea compound or a fast-acting insulin secretagogue fails to provide an insulin secretion effect and therefore, fails to provide a sufficient hypoglycemic effect.

This application is based on a patent application No. 2004-218736 filed in Japan, the contents of which are incorporated herein by reference.

The invention claimed is:

1. A method for treating type 2 diabetes with sulfonylurea secondary failure in a mammal, which comprises administering an effective amount of a compound represented by the formula:

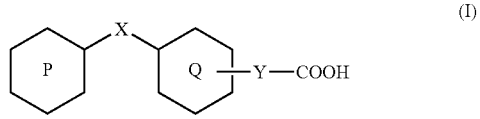

(I)

wherein ring P is an aromatic ring optionally having substituent(s), ring Q is an aromatic ring optionally further having substituent(s) besides —Y—COOH, and X and Y are each independently a spacer,
or a salt thereof, to the mammal.

2. The method of claim 1, wherein the sulfonylurea secondary failure is caused by a sulfonylurea compound.

3. The method of claim 1, wherein the sulfonylurea secondary failure is caused by a fast-acting insulin secretagogue.

4. The method of claim 1, wherein the compound is a compound represented by the formula

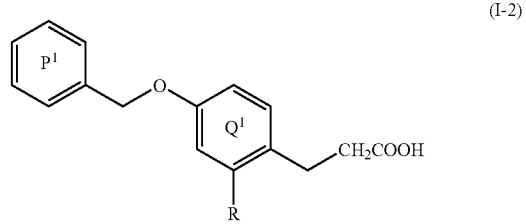

(I-2)

wherein ring $P^1$ is a benzene ring having substituent(s) having a benzene ring, ring $Q^1$ is a benzene ring optionally having substituent(s), and R is a hydrogen atom or a substituent;
or a salt thereof.

5. The method of claim 4, wherein
ring $P^1$ is a benzene ring having substituent(s) represented by the formula: $R^1$-$E^1$-, wherein $R^1$ is a phenyl group or an indanyl group, each optionally having substituent(s) selected from the group consisting of halogen atom, nitro group, carboxyl group, optionally halogenated $C_{1-6}$ alkyl group, hydroxy-$C_{1-6}$ alkyl group, carboxy-$C_{1-6}$ alkyl-carbonylamino-$C_{1-6}$ alkyl group, optionally halogenated $C_{1-6}$ alkoxy group, $C_{6-14}$ aryl group, $C_{6-14}$ aryloxy group and $C_{7-16}$ aralkyloxy group, and $E^1$ is a bond or a spacer selected from the group consisting of —O—, —CH$_2$—O—, —CO—, —CONH—, —N(CH$_3$)CH$_2$—, —S—CH$_2$— and —CH=CH—, and the benzene ring is optionally substituted by $C_{1-6}$ alkyl group;
ring $Q^1$ is a benzene ring optionally having $C_{1-6}$ alkyl group; and
R is a hydrogen atom.

* * * * *